United States Patent [19]

Sariaslani et al.

[11] Patent Number: 5,580,783
[45] Date of Patent: Dec. 3, 1996

[54] ENZYMATIC PROCESS FOR THE PREPARATION OF CHIRAL α-TERTIARY CARBOXYLIC ACID ESTERS

[75] Inventors: Fateme S. Sariaslani, Newark, Del.; Barry Stieglitz, Wynnewood, Pa.; Vincent G. Witterholt, Wilmington, Del.

[73] Assignee: E. I. Du Pont de Nemours and Company, Wilmington, Del.

[21] Appl. No.: 457,891

[22] Filed: Jun. 1, 1995

Related U.S. Application Data

[63] Continuation-in-part of Ser. No. 321,496, Oct. 12, 1994, abandoned.

[51] Int. Cl.$^6$ ............................................. C12P 41/00
[52] U.S. Cl. ............................................. 435/280
[58] Field of Search ................................... 435/280

[56] References Cited

U.S. PATENT DOCUMENTS

| | | | |
|---|---|---|---|
| 4,898,822 | 2/1990 | Asada et al. | 435/121 |
| 5,043,274 | 8/1991 | Reid et al. | 435/135 |
| 5,075,233 | 12/1991 | Bertola et al. | 435/280 |
| 5,108,916 | 4/1992 | Cobbs et al. | 435/135 |
| 5,108,917 | 4/1992 | Bertola et al. | 435/136 |
| 5,202,260 | 4/1993 | Yee et al. | 435/280 |
| 5,273,895 | 12/1993 | Rossi et al. | 435/136 |
| 5,300,437 | 4/1994 | Stirling et al. | 435/280 |
| 5,302,528 | 4/1994 | Battistel et al. | 435/280 |
| 5,322,791 | 6/1994 | Sih | 435/280 |
| 5,332,675 | 7/1994 | Minai et al. | 435/280 |
| 5,492,830 | 2/1996 | Kalwass et al. | 435/280 |

OTHER PUBLICATIONS

Sugai T. et al, J. Org. Chem. 55:4643–47 (1990).
Matta M. S., J. Am. Chem Soc. 94(24) 8573–8 (1972).
ATCC Catalogue of Bacteria & Bacteriophages p. 270 (1992).
ATCC Catalogue of Yeasts pp. 7, 11, 17, 99 (1990).
Brackenridge, I. et al, J. Chem. Soc. Perkin Trans., 1, 1093–1094 (1993).
Yanase, H., Biosci. Biotech. Biochem., 57(8), 1334–1337 (1993).
Feichter et al, J. Chem. Soc. Perkin Trans., 1, 653–654, (1991).
Peters, J. et al, Appl. Microbiol. Biotechnol., 38, 334–340, (1992).
Yee, C. et al, J. Org. Chem., 57, 3525–3527, (1992).

Primary Examiner—Michael G. Wityshyn
Assistant Examiner—S. Saucier

[57] ABSTRACT

This invention provides a process for enrichment of enantiomers of α-tertiary carboxylic acid esters from mixtures of corresponding esters using a biocatalyst comprising microbial cells, or partially or highly purified enzyme preparations. The enantiomeric ester products are useful as intermediates for the preparation of pharmaceutically and agriculturally active compounds.

11 Claims, No Drawings

ENZYMATIC PROCESS FOR THE PREPARATION OF CHIRAL α-TERTIARY CARBOXYLIC ACID ESTERS

This application is a continuation in part of application Ser. No. 08/321,496 filed Oct. 12, 1994, now abandoned.

BACKGROUND OF THE INVENTION

Many agrichemicals and pharmaceuticals are currently marketed as racemic or diastereomeric mixtures. In many cases, the desired physiological effect derives from only one enantiomer/diastereomer while the other enantiomer/diastereomer is inactive or even harmful or inhibitory. Chemical and enzymatic techniques for separating enantiomers are becoming increasingly important tools for production of chemicals of high enantiomer purity.

U.S. Pat. No. 4,898,822 describes the preparation of optically active indoline-2-carboxylic acids by hydrolysis of the corresponding racemic esters utilizing enzymes or microorganisms possessing stereoselective esterase activity. The substrates disclosed in that patent are compounds of the following general formula:

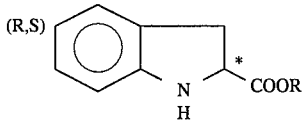

wherein the chiral center indicated by the asterisk is a secondary-substituted α-carbon atom.

U.S. Pat. No. 5,202,260 and Yee et at., *J. Org. Chem.* (1992) 57: 3525–3527, disclose preparation of optically active acids and their corresponding esters by partial enzymatic hydrolysis of α-tertiary carboxylic acid esters using enzymes derived from *Candida lipolytica*. The enzyme utilized is derived exclusively from a single species of yeast, and solely transforms the S-ester of the racemic mix into its corresponding S-acid, leaving the R-ester intact.

Feichter et at., in *J. Chem. Soc. Perkin Trans.* (1991) 1: 653–654, disclose stereospecific hydrolysis of racemic methyl atrolactate via the action of, inter alia, α-chymotrypsin, resulting in formation of the corresponding R-acid and S-ester.

Peters et at., in *Appl. Microbiol. Biotechnol.* (1992) 38: 334–340, describe the stereospecific reduction of keto acids or esters to produce their corresponding chiral hydroxy acids or esters. Specifically, these authors demonstrate stereospecific keto ester reductase activity of *Candida parapsilosis* and *Rhodococcus erythropolis* wherein a racemic, acyclic, β-keto acid ester is stereospecifically transformed into its corresponding chiral hydroxy acid ester.

SUMMARY OF THE INVENTION

This invention provides a process for enrichment of enantiomers of α-tertiary carboxylic acids or esters from mixtures of their corresponding esters by contacting said mixtures of esters with a biocatalyst comprising whole cells, or partially or highly purified enzyme preparations. The enantiomeric ester compounds are useful as intermediates for the preparation of pharmaceutically and agriculturally active compounds. For example, WO 92/11249 discloses methyl 5-chloro-2,3-dihydro-2-hydroxy-1-oxo-1H-indene-2-carboxylate as an intermediate for the preparation of certain arthropodicidal carboxanilides.

The invention particularly provides a process for preparation of an enantiomerically enriched carboxylic acid ester, which process comprises contacting a mixture of enantiomers of an ester of Formula I

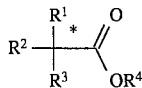

wherein:

$R^1$ and $R^2$ are independently selected from the group consisting of phenyl and $C_1$–$C_6$ alkyl, each group optionally substituted with up to 3 members of the group consisting of halogen, $C_1$–$C_3$ alkoxy, and phenoxy; provided that $R^1$ and $R^2$ are different from each other; or $R^1$, $R^2$ and the carbon to which they are attached are taken together to form the group

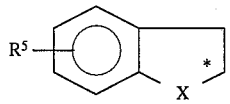

wherein:

X is selected from the group consisting of C=O, O, S and NH;

$R^3$ is selected from the group consisting of OH and $NH_2$;

$R^4$ is $C_1$–$C_6$ alkyl; and $R^5$ is selected from the group consisting of halogen and $C_1$–$C_3$ fluoroalkoxy, wherein the chiral carbon is indicated by an asterisk;

with a biocatalyst selected from the group consisting of IM60 Lipozyme; Chirazyme L-2 lipase; Chirazyme L-5 lipase; Chirazyme L-7 lipase; SP 524 lipase; SP 526 lipase; SP 539 protease; Lipolase Lipase; CR Lipase; *Corynebacterium hoagii* ATCC 7005; *Flavobacterium* sp. ATCC 27551; *Pseudomonas oleovorans* NRRL-B-3429; *Pseudomonas putida* ATCC 23973; *Pseudomonas* sp. NRRL-B-11330; *Rhodococcus equi* ATCC 14887; *Rhodococcus erythropolis* ATCC 4277; *Rhodococcus coprophilus* NRRL-B-16536; *Rhodococcus rhodnii* NRRL-B-16535; *Rhodococcus rhodochrous* ATCC 55602; *Rhodococcus* sp. NRRL-B-16531; *Rhodococcus* sp. NRRL-B-16534; *Streptomyces griseus* ATCC 6855; *Xanthomonas campestris* ATCC 21818; *Candida guilliermondii* ATCC 6260; *Candida kefyr* ATCC 4135; *Candida tropicalis* ATCC 46491; *Rhodotorula rubra* ATCC 4557; *Yarrowia lipolytica* ATCC 9773; *Aspergillus alliaceus* ATCC 10060; *Beauveria bassiana* ATCC 26037; *Beauveria bassiana* ATCC 74292; *Beauveria bassiana* ATCC 26851; *Beauveria bassiana* ATCC 38657; *Beauveria nivea* ATCC 74294; *Cunninghamella echinulata* ATCC 8688a; *Lophotrichus martinii* ATCC 11221; *Paecilomyces marquandi* ATCC 10525; *Pestalotia microspora* ATCC 11816; *Rhizopus oryzae* ATCC 10404; *Rhizopus oryzae* ATCC 22580; *Sporobolomyces* sp. ATCC 20290; *Trichophyton concentricum* ATCC 74293; *Bacillus cereus* NRRL-B-14591; *Nocardia* sp. NRRL-B-5646; *Pseudomonas putida* ATCC 17453; *Saccharomyces cerevisiae* NRRL-Y-2034; *Schizosaccharomyces ostosporus* NRRL-Y-854; *Aspergillus alliaceus* NRRL-315; *Penicillium chrysogenum* ATCC 10002; *Penicillium notatum* ATCC 36740; *Amycolatopsis rugosa* NRRL-B-2295; *Rhodococcus equi* ATCC 13556; *Streptomyces endus* NRRL-B-2339; *Aspergillus candidus* ATCC 20022; and *Mycotypha microspora* ATCC 8982.

Applicants have found that certain of the preferred biocatalysts of the invention are useful for enrichment of either the (+) or (−) enantiomer of two specifically preferred mixtures of enantiomers of esters: ethyl α-hydroxy- α-methyl-4-phenoxybenzene acetate:

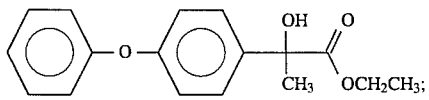

and methyl 5-chloro-2,3-dihydro-2-hydroxy-1-oxo-1H-indene-2-carboxylate:

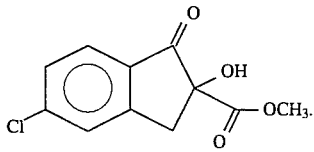

Postulated mechanisms of the invention for enantiospecific biotransformation comprise enantiospecific hydrolysis of one enantiomer of the mixture of α-tertiary esters to produce the corresponding carboxylic acid, and, in the case of mixtures of enantiomers of keto acid esters, enantiospecific reduction of the keto group resulting in formation of corresponding α-tertiary hydroxy-acid esters.

DETAILS OF THE INVENTION

This invention concerns a process for the preparation of enantiomerically enriched α-tertiary carboxylic acids or esters from starting substrates consisting of a mixture of enantiomers of their corresponding esters.

The starting compounds are mixtures of enantiomers of esters having an α-tertiary carbon, and are shown by Formula I:

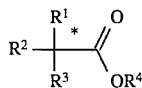   I wherein:
$R^1$ and $R^2$ are independently selected from the group consisting of phenyl and $C_1$–$C_6$ alkyl, each group optionally substituted with up to 3 members of the group consisting of halogen, $C_1$–$C_3$ alkoxy, and phenoxy; provided that $R^1$ and $R^2$ are different from each other; or $R^1$, $R^2$ and the carbon to which they are attached are taken together to form the group

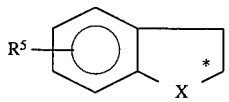

wherein:
X is selected from the group consisting of C=O, O, S and NH;
$R^3$ is selected from the group consisting of OH and $NH_2$;
$R^4$ is $C_1$–$C_6$ alkyl; and
$R^5$ is selected from the group consisting of halogen and $C_1$–$C_3$ fluoroalkoxy,
wherein the chiral carbon is indicated by an asterisk.

Preferred substrates are compounds of Formula I wherein:
$R^1$ is phenyl optionally substituted with phenoxy;
$R^2$ is $C_1$–$C_3$ alkyl; or $R^1$, $R^2$ and the carbon to which they are attached are taken together to form the group

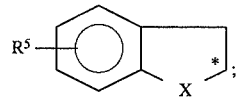

X is C(=O);
$R^3$ is OH;
$R^4$ is $C_1$–$C_3$ alkyl; and
$R^5$ is halogen.

Specifically preferred substrates are:
ethyl α-hydroxy-α-methyl-4-phenoxybenzene acetate; and
methyl 5-chloro-2,3-dihydro-2-hydroxy-1-oxo-1H-indene-2-carboxylate.

Substrates of this invention are readily prepared by techniques known to one skilled in the art. For example, ethyl α-hydroxy-α-methyl-4-phenoxybenzene acetate can be prepared as described below. A 250-mL flask fitted with magnetic stirring, water condenser, 125 mL dropping funnel, thermometer, and nitrogen inlet was charged with 2.7 g (110 mmol) of magnesium metal and dried with a heat gun under strong nitrogen purge. After cooling, the funnel was charged with a solution of 17.5 mL (24.9 g, 100 mmol) of 4-bromodiphenyl ether in 67 mL of dry THF, and 10 mL was run into the flask. With stirring, the Grignard initiated spontaneously, and the rest of the bromide solution was added over 15 min, maintaining an internal temperature of 67°–68° C. When addition was complete, the temperature held at 68° C. for 5 min, then began to drop, reaching 30° C. after 45 min. Meanwhile, a 250 mL flask, magnetic stirrer, and 125 mL dropping funnel that had been oven-dried were assembled hot under nitrogen and allowed to cool. A low-temperature thermometer was then added, the flask was charged with a solution of 11.5 mL (12.2 g, 105 mmol) of ethyl pyruvate in 66 mL of dry THF, and the solution of Grignard reagent was transferred to the dropping funnel by means of a syringe. The pyruvate solution was chilled to −10° C., and the Grignard solution was run in over 15 min with good stirring, cooling to maintain an internal temperature of −5° to −10° C. The resulting solution was stirred and treated with 50 mL of water followed by 50 mL of saturated aqueous ammonium chloride, giving two clear phases. These were separated, and the upper phase was subjected to rotary evaporation to remove most of the THF. Addition of 50 mL portions of water and methylene chloride gave two clear phases. These were separated, the aqueous phase was washed with another 25 mL of methylene chloride, and the combined organic phases were washed with water and brine, dried over magnesium sulfate, and evaporated to leave 23.8 g of yellow-orange oil. Kugelrohr distillation at 140° C./0.1–0.2 mM for 60 min removed volatile impurities, leaving 17.1 g (60%) of the product as a clear orange oil.

Likewise, methyl 5-chloro-2,3-dihydro-2-hydroxy-1-oxo-1H-indene-2-carboxylate can be prepared by the following protocol. Sodium hydride (24 g of 60% solution in oil, 0.6 mol) was washed with hexanes to remove the oil. The resulting washed NaH was suspended in 200 mL of DMF and then treated with a solution of 50 g (0.3 mol) of 5-chloro-1-indanone and 150 mL of DMF at such a rate that reaction temperature remained below 35° C. The resulting mixture was stirred for 30 min and then treated with 38 mL (0.45 mol) of dimethyl carbonate added over 15 min. The resulting mixture was stirred at room temperature for 1.5 h and then allowed to stand overnight. The reaction mixture was poured carefully into a mixture of 100 mL of concentrated HCl and about 1000 mL of ice. Then, 500 mL of ether was added and the aqueous layer was extracted twice with ether. The combined organic layers were washed with three portions of $H_2O$, dried ($MgSO_4$) and concentrated to give 64.6 g of a brown oil. A solution of 5.0 g (0.022 mol) of the above product and 70 mL of methylene chloride was treated with 10 g (ca. 0.032 mol) of 50–60% m-chloroperbenzoic acid (Aldrich) at room temperature. After 1 h, the reaction was cooled to 0° C. and quenched by careful addition of saturated aqueous sodium carbonate. The layer was washed twice with saturated aqueous sodium carbonate, once with saturated sodium bisulfite, dried ($MgSO_4$) and concentrated to give 4.0 g of a yellow solid.

In one embodiment of the present invention, biocatalytic action of the disclosed enzymes and biological materials results in conversion of the undesired enantiomer into products that are readily separable from the unaffected enantiomer. In the context of the present disclosure, efficiency of the instant preparative process has been measured by quantifying 1) the degree of recovery and 2) the enantiomeric purity of the desired product(s). The degree of recovery is that percent of the starting substrate remaining following biocatalytic treatment. Enantiomeric purity of the desired product is determined by calculation of the excess of the desired enantiomer over the unwanted enantiomer remaining in the recovered substrate following biocatalytic treatment. This enantiomer excess (% e.e.) is calculated from the concentration of the individual enantiomers using one of the following equations:

$$\% \text{ e.e. of the } (+) \text{ form} = ([(+)] - [(-)])/([(+)] + [(-)]) \times 100$$

$$\% \text{ e.e. of the } (-) \text{ form} = ([(-)] - [(+)])/([(-)] + [(+)]) \times 100$$

wherein $[(+)]$ and $[(-)]$ are the concentrations of the $(+)$ and $(-)$ forms, respectively. Although it is not an essential aspect of the present process, if desired, the enantiomerically enriched ester product (defined as $\geq 50\%$ e.e.) may be separated from the biocatalytic reaction mixture by any of several means well known in this art.

For purposes of the present invention, mixtures of enantiomers that serve as substrates for the disclosed processes are mixtures of enantiomeric esters wherein the % e.e. is less than 50. This necessarily includes racemix mixtures wherein both enantiomers are present in equal proportions, as well as optically active mixtures wherein one enantiomer is present in excess over its complimentary enantiomer, but wherein the enantiomeric excess is less than 50%. In either case, the process of the instant invention results in preparation of an enantiomerically enriched carboxylic acid ester wherein the desired enantiomer has been obtained to a % e.e. of at least 50.

For purposes of the present disclosure, Applicants intend that the following terms convey the meaning set forth below.

The term "enantiomerically enriched" means that the desired enantiomer has been obtained to a % e.e. of at least 50.

The term "biocatalyst" includes enzymatic activity provided by whole bacteria, yeast or fungal cells or cell extracts or products; or enzymatic activity in purified or partially purified form from bacterial, yeast, fungal or mammalian cells, which enzymatically catalyzes the reaction process of the present invention.

Those biocatalysts yielding an enantiomeric excess greater than 50% (representing greater than a 3-fold excess of the desired enantiomer over the other enantiomeric species remaining) are preferred. More preferred is enrichment above about 90%, even more preferred above about 95%, and most preferred above about 99%.

In the course of experimentation, the inventors evaluated more than four hundred potential sources of biocatalysts. Surprisingly, those disclosed herein possessed the activity sought by the inventors. Therefore, this invention is particularly characterized by the biocatalysts (microorganisms or mutants thereof, or enzymes) capable of carrying out the enantiospecific reaction(s). Preferred biocatalysts comprise those derived from the following microorganisms: *Corynebacterium hoagii* ATCC 7005; *Flavobacterium sp.* ATCC 27551; *Pseudomonas oleovorans* NRRL-B-3429; *Pseudomonas putida* ATCC 23973; *Pseudomonas sp.* NRRL-B-11330; *Rhodococcus equi* ATCC 14887; *Rhodococcus erythropolis* ATCC 4277; *Rhodococcus coprophilus* NRRL-B-16536; *Rhodococcus rhodnii* NRRL-B-16535; *Rhodococcus rhodochrous* ATCC 55602; *Rhodococcus sp.* NRRL-B-1653 1; *Rhodococcus sp.* NRRL-B-16534; *Streptomyces griseus* ATCC 6855; *Xanthomonas campestris* ATCC 21818; *Candida guilliermondii* ATCC 6260; *Candida kefyr* ATCC 4135; *Candida tropicalis* ATCC 46491; *Rhodotorula rubra* ATCC 4557; *Yarrowia lipolytica* ATCC 9773; *Aspergillus alliaceus* ATCC 10060; *Beauveria bassiana* ATCC 26037; *Beauveria bassiana* ATCC 74292; *Beauveria bassiana* ATCC 26851; *Beauveria bassiana* ATCC 38657; *Beauveria nivea* ATCC 74294; *Cunninghamella echinulata* ATCC 8688a; *Lophotrichus martinii* ATCC 11221; *Paecilomyces marquandi* ATCC 10525; *Pestalotia microspora* ATCC 11816; *Rhizopus oryzae* ATCC 10404; *Rhizopus oryzae* ATCC 22580; *Sporobolomyces sp.* ATCC 20290; *Trichophyton concentricum* ATCC 74293; *Bacillus cereus* NRRL-B-14591; *Nocardia sp.* NRRL-B-5646; *Pseudomonas putida* ATCC 17453; *Saccharomyces cerevisiae* NRRL-Y-2034; *Schizosaccharomyces ostosporus* NRRL-Y-854; *Aspergillus alliaceus* NRRL-315; *Penicillium chrysogenum* ATCC 10002; *Penicillium notatum* ATCC 36740; *Amycolatopsis rugosa* NRRL-B-2295; *Rhodococcus equi* ATCC 13556; *Streptomyces endus* NRRL-B-2339; *Aspergillus candidus* ATCC 20022; and *Mycotypha microspora* ATCC 8982. The biological material comprising the enantiospecific enzymes capable of carrying out the process of the invention can be isolated or biosynthesized and used as such, but it is usually more convenient to employ the appropriate microorganism(s) directly.

Also preferred are purified preparations of hydrolytic enzymes from the following sources: α-chymotrypsin (from Bovine Pancreas; Sigma Chemical Co.); β-chymotrypsin (from Bovine Pancreas; Sigma Chemical Co.); γ-chymotrypsin (from Bovine Pancreas; Sigma Chemical Co.); δ-chymotrypsin (from Bovine Pancreas; Sigma Chemical Co.); IM60 Lipozyme (from *Mucor miehei*; Novo Nordisk); Chirazyme L-2 lipase (from *Candida antarctica* Fraction B; Boehringer Mannheim); Chirazyme L-5 lipase (from *Candida antarctica* Fraction A; Boehringer Mannheim); Chirazyme L-7 lipase (source not specified; Boehringer Mannheim); SP 524 lipase (from *Mucor sp.*; Novo Nordisk); SP 526 lipase (from *Candida antarctica* Fraction A; Novo Nordisk); SP 539 protease (from *Bacillus sp.*; Novo Nordisk); Lipolase lipase (source not specified; Novo Nordisk); and CR Lipase (from *Candida rugosa*; Altus Biologics, Inc.).

Most preferred are biocatalysts comprising those found in the following microorganisms: *Rhodococcus rhodochrous* ATCC 55602; *Trichophyton concentricum* ATCC 74293; *Beauveria bassiana* ATCC 74292; and *Beauveria nivea* ATCC 74294.

In this method for enriching mixtures of enantiomers of α-tertiary carboxylic acid esters for either the (+)- or (−)-enantiomer, biocatalysis is accomplished by the action of one or more enantiospecific enzymes which are conveniently obtained by culturing the microorganism in a medium suitable for production of the enantiospecific enzyme. The enzyme thus obtained is added to selectively act upon either the (+)- or (−)-α-tertiary carboxylic acid ester of the mixture, which results in enrichment of the remaining (+)- or (−)-carboxylic acid ester. The desired product (the enriched carboxylic acid ester) can then be separated from the undesired products (the (+) or (−) carboxylic acid or (+)- or (−)-hydroxy acid ester) by methods known to one skilled in the art for separating carboxylic acid esters from acids, keto acid esters from hydroxy acid esters, and for separating individual enantiomers. Obviously, Applicants recognize that the method of the invention could also be equally well described as a process for enantiomeric enrichment of (+) or (−) α-tertiary carboxylic acids or (+) or (−) hydroxy acid esters, via the selective biocatalysis of the corresponding mixture of enantiomers of α-tertiary carboxylic acid ester.

The biocatalysts of the present invention comprise biological materials derived from or located in bacterial, yeast, fungal and mammalian cells. Several of these biocatalysts have been deposited under the terms of the Budapest Treaty at ATCC (American Type Culture Collection, 12301 Parklawn Drive, Rockville, Md. 20852), and bear the following accession numbers:

| Biocatalyst | Accession Number |
| --- | --- |
| Rhodococcus rhodochrous | ATCC 55602 |
| Trichophyton concentricum | ATCC 74293 |
| Beauveria bassiana | ATCC 74292 |
| Beauveria nivea | ATCC 74294 |

The following abbreviations are employed herein:
MCIC—Methyl 5-chloro-2,3-dihydro-2-hydroxy-1-oxo-1H-indene-2-carboxylate
EHPA—Ethyl α-hydroxy-α-methyl-4-phenoxybenzene acetate
HPLC—High Performance Liquid Chromatography
DMF—Dimethyl Formamide
ACN—Acetonitrile
e.e.—Enantiomer Excess
SM—Sabouraud Maltose Broth
SBG—Soybean Glycerol
NB—Nutrient Broth
PD—Potato Dextrose Broth For determination of biocatalytic activity, 25 mL of an appropriate growth medium was inoculated with a small portion of a frozen or lyophilized stock of test organism using standard microbiological techniques. Media utilized for growth of the organisms disclosed in the instant specification was chosen from the following:
SM (Sabouraud Maltose Broth; BBL Inc., Cockeysville, Md.);
PD (Potato Dextrose Broth; Difco Laboratories, Inc., Detroit, Mich.);
NB (Nutrient Broth; Difco Laboratories, Inc., Detroit, Mich.);

| SBG (Soybean Glycerol) (pH 7.0) | grams/liter |
| --- | --- |
| Glycerol | 20.0 |
| Yeast Extract | 5.0 |
| Soybean Flour | 5.0 |
| Sodium Chloride | 5.0 |
| Potassium Phosphate (dibasic) | 5.0. |

Growth medium employed for each disclosed microorganism is indicated in Tables 1–6. Inoculated cultures were grown for 72 h at 28°–30° C. with constant shaking (250 rpm; Stage I growth). Ten to twenty percent of this starter culture was transferred to fresh medium (25 mL), and incubation continued for an additional 24 h (Stage II growth). Cells were harvested and resuspended in a suitable buffer (pH 4.5–8.5) wherein the final concentration of the biocatalyst was about 10–250 mg of catalyst (dry weight) per mL of buffer, and the final concentration of substrate was about 2–200 mM. Incubation to achieve biotransformation was continued for 4–72 h at 25°–50° C. with constant shaking (250 rpm). The reactions were then acidified and extracted with methylene chloride. Following $CH_2Cl_2$ evaporation, the residues were resuspended in ACN. The percent recovery of substrate in the ACN solution was determined by reverse-phase HPLC, and enantiomeric purity was determined by chiral HPLC.

ANALYTICAL PROCEDURES

Tertiary α-substituted carboxylic acid esters and hydrolysis products were measured by reverse phase HPLC. Detection was by ultra-violet light absorption. For MCIC, a Zorbax® RX-$C_8$ column (4.6×250 mM) employing a mobile phase of 40% acetonitrile and 60% $H_2O$+0.1% triethylamine (adjusted to pH 6.5) was used. For EHPA, a Zorbax® $C_{18}$ column (4.6×250 mM) employing a mobile phase of 50% acetonitrile and 50% $H_2O$ acidified with 0.1% $H_3PO_4$ was used. Chromatographic identity and quantitation of esters was determined by comparison with authentic standards.

Chiral HPLC for the separation of enantiomers is carried out with an α-acid glycoprotein column obtained from Chromatech (Sweden). The mobile phases for separation of the ester enantiomers are summarized below.

| Enantiomers | Mobile Phase |
| --- | --- |
| MCIC | 98% 0.01M phosphate buffer (pH 4.8):2% ethanol |
| EHPA | 91% $H_2O$ + 0.1% triethylamine (pH 6.0):9% acetonitrile |

Chiral HPLC for the separation of EHPA enantiomers in Example 10 was carried out with a Bakerbond® chiral OD column obtained from J. T. Baker. The mobile phase for separation of EHPA enantiomers was 90% hexane: 10% propanol.

Enantiomeric composition, purity and chromatographic identity of the above esters was determined by comparison with authentic standards of enantiomers or racemic mixtures.

EXAMPLE 1

For the microbial strains listed in Table 1, cells were harvested from Stage II growth by centrifugation and resuspended in 5 mL of 50 mM phosphate buffer, pH 6.0 (50–100 mg wet weight cells/mL buffer). Then, 10 μmol of racemic MCIC in 50 μL DMF was added. After incubation at 30° C. for 24 h, reactions were terminated (2 mM biotransformations) or another 10 μmol of racemic MCIC in 50 μL DMF was added and the incubation continued for another 24 h (4 mM biotransformation). Both 2 mM and 4 mM MCIC biotransformations were terminated by acidification to pH 3 with 3 M $H_2SO_4$. Two volumes of methylene chloride were added to each sample and the suspensions were agitated for 15 min. The methylene chloride layers were removed and evaporated to dryness under a stream of nitrogen, and the residues were resuspended in 10 mL acetonitrile. The percent of both MCIC recovered and (+)-MCIC e.e. were determined by reverse-phase HPLC and chiral HPLC, respectively, and the results are shown in Table 1.

EXAMPLE 2

A 10 mg sample of each chymotrypsin enzyme (Table 1 ) was added to 2 mL of 50 mM phosphate buffer pH 6.0. Then 4 μmol of racemic MCIC in 20 μL DMF was added. Similarly, a 20 mg sample of Chirazyme L-7 lipase was added to 50 mM phosphate buffer pH 6.0 and 40 μmol of racemic MCIC in 20 μL DMF was added. After 24 h incubation at 30° C., (chymotrypsins) or 25° C. (L-7) and following the same extraction and analytical procedures as in Example 1, the percent MCIC recovered and (+)-MCIC e.e. were determined. The results are shown in Table 1.

MCIC recovered and (−)-MCIC e.e. were determined. The results are shown in Table 2.

EXAMPLE 4

Five mg of Chirazyme L-2 lipase, 10 mg of SP 524 lipase, SP 526 lipase, SP 539 protease or 20 mg of Chirazyme L-5 lipase (Table 2) was added to 2 mL of 50 mM phosphate

TABLE 1

Enantiomer Enrichment of
(+)-Methyl 5-chloro-2,3-dihydro-2-hydroxy-1-oxo-1H-indene-2-carboxylate

| Strain | Growth Medium | Incubation Time (h) | Substrate mM Added | % Recovered | % e.e. |
|---|---|---|---|---|---|
| *Corynebacterium hoagii* ATCC 7005 | SM | 48 | 4 | 53 | 50 |
| *Flavobacterium* sp. ATCC 27551 | SM | 48 | 4 | 47 | 52 |
| *Pseudomonas oleovorans* NRRL-B-3429 | SBG | 24 | 2 | 19 | 100 |
| *Pseudomanas putida* ATCC 23973 | NB | 24 | 2 | 49 | 60 |
| Pseudomonas sp. NRRL-B-11330 | SBG | 48 | 4 | 14 | 64 |
| *Rhodococcus equi* ATCC 14887 | NB | 48 | 4 | 29 | 80 |
| *Rhodococcus erythropolis* ATCC 4277 | SBG | 48 | 4 | 21 | 82 |
| *Rhodococcus coprophilus* NRRL-B-16536 | SBG | 48 | 4 | 33 | 100 |
| *Rhodococcus rhodnii* NRRL-B-16535 | SBG | 48 | 4 | 15 | 100 |
| *Rhodococcus rhodochrous* ATCC 55602 | SBG | 48 | 4 | 35 | 98 |
| Rhodococcus sp. NRRL-B-16534 | SBG | 48 | 4 | 14 | 66 |
| *Streptomyces griseus* ATCC 6855 | SBG | 48 | 4 | 33 | 66 |
| *Xanthomonas campestris* ATCC 21818 | SBG | 48 | 4 | 36 | 100 |
| *Rhodotorula rubra* ATCC 4557 | SBG | 48 | 4 | 37 | 86 |
| *Beauveria bassiana* ATCC 74292 | PD | 48 | 4 | 41 | 92 |
| *Beauveria bassiana* ATCC 26851 | PD | 48 | 4 | 31 | 100 |
| *Cunninghamella echinulata* ATCC 8688[a] | PD | 24 | 2 | 36 | 50 |
| *Paecilomyces marquandi* ATCC 10525 | SM | 48 | 4 | 52 | 60 |
| *Pestalotia microspora* ATCC 11816 | PD | 48 | 4 | 20 | 50 |
| *Rhizopus oryzae* ATCC 10404 | PD | 48 | 4 | 49 | 100 |
| *Rhizopus oryzae* ATCC 22580 | PD | 48 | 4 | 48 | 100 |
| *Trichophyton concentricum* ATCC 74293 | PD | 48 | 4 | 20 | 92 |
| α-Chymotrypsin (Sigma) | NA[a] | 24 | 2 | 46 | 100 |
| β-Chymotrypsin (Sigma) | NA | 24 | 2 | 45 | 100 |
| γ-Chymotrypsin (Sigma) | NA | 24 | 2 | 30 | 100 |
| δ-Chymotrypsin (Sigma) | NA | 24 | 30 | 60 | 72 |
| Chirazyme L-7 lipase (Boehringer Mannheim) | NA | 24 | 20 | 34 | 80 |

[a]NA - Not Applicable

EXAMPLE 3

For the microbial strains listed in Table 2, cells were harvested from Stage II growth by centrifugation and resuspended in 5 mL of 50 mM phosphate buffer pH 6.0 (50–100 mg wet weight cells/mL buffer). In the same manner as in Example 1, 10 μmol of racemic MCIC was added. Following the same incubation (4 mM biotransformation), extraction and analytical procedures as in Example 1, the percent buffer pH 6.0. Then 40 μmol of racemic MCIC (20 μmol for SP526) in 20 μL DMF was added. After 24 h incubation at 25° C. and following the same extraction and analytical procedures as in Example 1, the percent MCIC recovered and (−)-MCIC e.e. were determined. The results are shown in Table 2.

TABLE 2

Enantiomer Enrichment of
(−)-Methyl 5-chloro-2,3-dihydro-2-hydroxy-1-oxo-1H-indene-2-carboxylate

| Strain | Growth Medium | Incubation Time (h) | Substrate mM Added | % Recovered | % e.e. |
|---|---|---|---|---|---|
| *Candida guilliermondii* ATCC 6260 | SM | 48 | 4 | 33 | 100 |
| *Candida kefyr* ATCC 4135 | SM | 48 | 1 | ND[a] | 50 |
| *Candida tropicalis* ATCC 46491 | SM | 48 | 4 | 29 | 76 |
| *Yarrowia lipolytica* ATCC 9773 | SM | 48 | 4 | 32 | 50 |
| *Aspergillus alliaceus* ATCC 10060 | SM | 48 | 1 | ND | 100 |
| *Beauveria nivea* ATCC 74294 | PD | 48 | 4 | 38 | 86 |
| *Lophotrichus martinii* ATCC 11221 | PD | 48 | 4 | 36 | 100 |
| Sporobolomyces sp. ATCC 20290 | PD | 48 | 4 | 45 | 100 |

TABLE 2-continued

Enantiomer Enrichment of
(−)-Methyl 5-chloro-2,3-dihydro-2-hydroxy-1-oxo-1H-indene-2-carboxylate

| Strain | Growth Medium | Incubation Time (h) | Substrate | | % e.e. |
|---|---|---|---|---|---|
| | | | mM Added | % Recovered | |
| SP 524 lipase (Novo Nordisk) | NA[b] | 24 | 20 | 16 | 66 |
| SP 526 lipase (Novo Nordisk) | NA | 24 | 10 | 22 | 85 |
| SP 539 protease (Novo Nordisk) | NA | 24 | 20 | 40 | 68 |
| Chirazyme L-2 lipase (Boehringer Mannheim) | NA | 24 | 20 | 13 | 100 |
| Chirazyme L-5 lipase (Boehringer Mannheim) | NA | 24 | 20 | 14 | 80 |

[a]ND - Not Determined
[b]NA - Not Applicable

EXAMPLE 5

For the microbial strains listed in Table 3, 42 μmol racemic MCIC in 100 μl DMF was added to each 24 h Stage II culture (25 mL SBG medium). Following MCIC addition, 4 mL aliquots are removed from the broths after 8 h or 29 h incubation at 27° C. One mL of ethylacetate was added to each sample and the suspensions were agitated for 10 seconds. Two-tenths mL of the ethylacetate layer was removed from each sample, evaporated to dryness under a stream of nitrogen and residues were resuspended in 3 mL of acetonitrile. The percent MCIC recovered and (−)-MCIC e.e. were determined by reverse-phase HPLC and chiral HPLC, respectively, and the results are shown in Table 3.

TABLE 3

Enantiomer Enrichment of
(−)-Methyl 5-chloro-2,3-dihydro-2-hydroxy-1-oxo-1H-indene-2-carboxylate

| Strain | Growth Medium | Incubation Time (h) | Substrate | | % e.e. |
|---|---|---|---|---|---|
| | | | mM Added | % Recovered | |
| Bacillus cereus NRRL-B-14591 | SBG | 29 | 1.7 | 27 | 48 |
| Nocardia sp. NRRL-B-5646 | SBG | 29 | 1.7 | 12 | 60 |
| Pseudomonas putida ATCC 17453 | SBG | 29 | 1.7 | 19 | 46 |
| Saccharomyces cerevisiae NRRL-Y-2034 | SBG | 29 | 1.7 | 35 | 78 |
| Schizosaccharomyces ostosporus NRRL-Y-854 | SBG | 8 | 1.7 | 30 | 98 |
| Aspergillus alliaceus NRRL-315 | SBG | 29 | 1.7 | 12 | 64 |
| Penicillium chrysogenum ATCC 10002 | SBG | 8 | 1.7 | 38 | 50 |
| Penicillium notatum ATCC 36740 | SBG | 29 | 1.7 | 19 | 46 |

EXAMPLE 6

For the microbial strains tested in Table 4, cells were harvested from Stage II growth by centrifugation and resuspended in 5 mL of 50 mM phosphate buffer pH 6.0 (50–100 mg wet weight cells/mL buffer). Then 10 μmol of racemic EHPA in 50 μL DMF was added. After incubation at 30° C. for 24 h, the reactions were terminated (2 mM biotransformation) or another 10 μmol of racemic EHPA in 50 μL DMF was added and the incubation continued for another 24 h (4 mM biotransformation). Both 2 mM and 4 mM EHPA biotransformations were terminated by acidification to pH 3 with 3M $H_2SO_4$. Two volumes of methylene chloride were added to each sample and the suspensions were agitated for 15 min. The methylene chloride layers were removed and evaporated to dryness under a stream of nitrogen, and the residues were resuspended in 10 mL acetonitrile. Both percent EHPA recovered and (+) - EHPA e.e. were determined by reverse phase HPLC and chiral HPLC, respectively, and the results are shown in Table 4.

EXAMPLE 7

A 20 mg sample of IM60 Lipozyme, SP 524 lipase, SP 526 lipase, or 1 mL of Lipolase lipase was added to 2 mL of 50 mM phosphate buffer pH 6.0 (1 mL for Lipolase). Then 20 μmol of racemic EHPA in 20 μL DMF was added. After 48 h incubation at 30° C. (IM60 Lipozyme) or 24 h at 25° C. (SP 525, SP 526, Lipolase), reactions were terminated by acidification to pH 3 with 3 M $H_2SO_4$. Following the same extraction and analytical procedures as in Example 6, percent EHPA and (+)-EHPA e.e. were determined. The results are shown in Table 4.

TABLE 4

Enantiomer Enrichment of
(+)-Ethyl α-hydroxy-α-methyl-4-phenoxybenzene acetate

| Strain | Growth Medium | Incubation Time (h) | Substrate mM Added | % Recovered | % e.e. |
|---|---|---|---|---|---|
| Pseudomonas sp. NRRL-B-11330 | SBG | 24 | 2 | 52 | 86 |
| Rhodococcus equi ATCC 13556 | SBG | 24 | 2 | 40 | 88 |
| Candida tropicalis ATCC 46491 | SM | 24 | 2 | 87 | 42 |
| Aspergillus candidus ATCC 20022 | SM | 24 | 2 | 48 | 24 |
| Beauveria bassiana ATCC 26851 | PD | 24 | 2 | 43 | 90 |
| Beauveria bassiana ATCC 38657 | PD | 24 | 2 | 28 | 100 |
| Mycolypha microspora ATCC 8982 | PD | 48 | 4 | 44 | 40 |
| Tricophyton concentricum ATCC 74293 | PD | 48 | 4 | 39 | 100 |
| IM60 Lipozyme (Novo Nordisk) | NA[a] | 48 | 10 | 47 | 84 |
| SP 524 lipase (Novo Nordisk) | NA | 24 | 10 | 10 | 60 |
| SP 526 lipase (Novo Nordisk) | NA | 24 | 10 | 36 | 51 |
| Lipolase lipase (Novo Nordisk) | NA | 24 | 10 | 22 | 50 |

[a]NA - Not Applicable

EXAMPLE 8

For the two microbial strains listed in Table 5, cells were harvested from Stage II growth by centrifugation and resuspended in 5 mL of 50 mM phosphate buffer pH 6.0 (50–100 mg wet weight cells/mL buffer). In the same manner as in Example 5, 10 µmol of racemic EHPA was added. Following the same incubation (2 mM biotransformation), extraction and analytical procedures as in Example 5, percent EHPA recovered and (−)- EHPA e.e. were determined. The results are shown in Table 5.

buffer). The cell suspensions were added to reaction vials containing 100 µmol of 50% e.e., (+)-MCIC. After incubation at 30° C. for 24 h, reactions were terminated by acidification to pH 3 with 3 M $H_2SO_4$. Five volumes of methylene chloride were added to each sample and the suspensions were agitated for 15 min. One-half of each methylene chloride layer was removed and evaporated to dryness under a stream of nitrogen and the residues were resuspended in 10 mL of acetonitrile. The percent of both MCIC recovered and (+)-MCIC e.e. were determined by reverse-phase HPLC and chiral HPLC, respectively, and the results are shown in Table 6.

TABLE 5

Enantiomer Enrichment of
(−)-Ethyl α-hydroxy-α-methyl-4-phenoxybenzene acetate

| Strain | Growth Medium | Incubation Time (h) | Substrate mM Added | % Recovered | % e.e. |
|---|---|---|---|---|---|
| Amycolatopsis rugosa NRRL-B-2295 | SM | 24 | 2 | 38 | 50 |
| Streptomyces endus NRRL-B-2339 | SBG | 24 | 2 | 12 | 82 |

EXAMPLE 9

For the microbial strains listed in Table 6, cells harvested from Stage II growth by centrifugation and stored frozen at −80° C. were thawed and resuspended in 2 mL of 50 mM phosphate buffer pH 6.0 (150–300 mg wet weight cells/mL

TABLE 6

Enantiomer Enrichment of 50% e.e., (+)-Methyl-5-chloro-2,3-dihydro-2-hydroxy-1-oxo-1H-indene-2-carboxylate

| Strain | Growth Medium | Cell Conc. (g/mL) | Incubation Time (h) | Substrate mM Added | % Recovered | % e.e. |
|---|---|---|---|---|---|---|
| Rhodococcus sp. NRRL-B-16531 | SBG | 0.30 | 24 | 50 | 67 | 82 |
| Rhodococcus sp. NRRL-B-16534 | SBG | 0.30 | 24 | 50 | 82 | 82 |
| Rhodococcus rhodochrous ATCC 55602 | SBG | 0.30 | 24 | 50 | 67 | 86 |
| Tricophyton concentricum ATCC 74293 | PD | 0.16 | 24 | 50 | 77 | 76 |
| Beauveria bassiana ATCC 26037 | PD | 0.29 | 24 | 50 | 82 | 76 |
| No Cells | — | — | 24 | 50 | 100 | 50 |

EXAMPLE 10

Ten mg of CR Lipase (Altus Biologics Inc., Cambridge, Mass.) was added to 2 mL of 50 mM phosphate buffer pH 6.0. Then 10 μmol of racemic EHPA in 20 μmol DMF was added. After 24 h incubation at 30° C., reactions were terminated by acidification to pH 3 with 3M $H_2SO_4$. Five volumes of methylene chloride were added to each sample and the suspensions were agitated for 15 min. One-half of each methylene chloride layer was removed and evaporated to dryness under a stream of nitrogen and the residues were resuspended in 10 mL of acetonitrile. The percent of both EHPA recovered and (+)-EHPA were determined by reverse-phase HPLC and chiral HPLC., respectively, and the results are shown in Table 7.

TABLE 7

Enantiomer Enrichment of
(+)-Ethyl α-hydroxy-α-methyl-4-phenoxybenzene acetate

| | | Substrate | | |
|---|---|---|---|---|
| Enzyme | Incubation Time (h) | mM Added | % Recovered | % e.e. |
| CR lipase (Altus Biologics) | 24 | 5 | 38 | 90 |

We claim:

1. A process for preparation of a mixture enriched in one enantiomer of a carboxylic acid ester which comprises contacting a mixture of enantiomers of an ester of Formula I

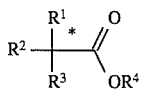

wherein:

$R^1$ and $R^2$ are independently selected from the group consisting of phenyl and $C_1$–$C_6$ alkyl, each group optionally substituted with up to 3 members of the group consisting of halogen, $C_1$–$C_3$ alkoxy, and phenoxy; provided that $R^1$ and $R^2$ are different from each other; or $R^1$, $R^2$ and the carbon to which they are attached are taken together to form the group

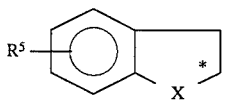

wherein:

X is selected from the group consisting of C=O, O, S and NH;

$R^3$ is selected from the group consisting of OH and $NH_2$;

$R^4$ is $C_1$–$C_6$ alkyl; and $R^5$ is selected from the group consisting of halogen and $C_1$–$C_3$ fluoroalkoxy, wherein the chiral carbon is indicated by an asterisk;

with a biocatalyst selected from the group consisting of IM60 Lipozyme; Chirazyme L-2 lipase; Chirazyme L-5 lipase; Chirazyme L-7 lipase; SP 524 lipase; SP 526 lipase; SP 539 protease; Lipolase Lipase; CR Lipase; *Corynebacterium hoagii* ATCC 7005; *Flavobacterium* sp. ATCC 27551; *Pseudomonas oleovorans* NRRL-B-3429; *Pseudomonas putida* ATCC 23973; *Pseudomonas* sp. NRRL-B-11330; *Rhodococcus equi* ATCC 14887; *Rhodococcus erythropolis* ATCC 4277; *Rhodococcus coprophilus* NRRL-B-16536; *Rhodococcus rhodnii* NRRL-B-16535; *Rhodococcus rhodochrous* ATCC 55602; *Rhodococcus* sp. NRRL-B-16531; *Rhodococcus* sp. NRRL-B-16534; *Streptomyces griseus* ATCC 6855; *Xanthomonas campestris* ATCC 21818; *Candida guilliermondii* ATCC 6260; *Candida kefyr* ATCC 4135; *Candida tropicalis* ATCC 46491; *Rhodotorula rubra* ATCC 4557; *Aspergillus alliaceus* ATCC 10060; *Beauveria bassiana* ATCC 26037; *Beauveria bassiana* ATCC 74292; *Beauveria bassiana* ATCC 26851; *Beauveria bassiana* ATCC 38657; *Beauveria nivea* ATCC 74294; *Cunninghamella echinulata* ATCC 8688; *Lophotrichus martinii* ATCC 11221; *Paecilomyces marquandi* ATCC 10525; *Pestalotia microspora* ATCC 11816; *Rhizopus oryzae* ATCC 10404; *Rhizopus oryzae* ATCC 22580; *Sporobolomyces* sp. ATCC 20290; *Trichophyton concentricum* ATCC 74293; *Bacillus cereus* NRRL-B-14591; *Nocardia* sp. NRRL-B-5646; *Pseudomonas putida* ATCC 17453; *Schizosaccharomyces ostosporus* NRRL-Y-854; *Aspergillus alliaceus* NRRL-315; *Penicillium chrysogenum* ATCC 10002; *Penicillium notatum* ATCC 36740; *Amycolatopsis rugosa* NRRL-B-2295; *Rhodococcus equi* ATCC 13556; *Streptomyces endus* NRRL-B-2339; *Aspergillus candidus* ATCC 20022; and *Mycotypha microspora* ATCC 8982.

2. The process according to claim 1 where in Formula I, $R^1$ is phenyl optionally substituted with phenoxy;

$R^2$ is $C_1$–$C_3$; or $R^1$, $R^2$ and the carbon to which they are attached are taken together to form the group

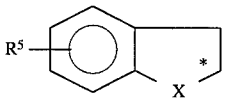

wherein:

X is C(=O);

$R^3$ is OH;

$R^4$ is $C_1$–$C_3$ alkyl; and $R^5$ is halogen.

3. The process of claim 2 wherein the mixture of enantiomeric esters of Formula I is methyl 5-chloro-2,3-dihydro-2-hydroxy-1-oxo-1H-indene-2-carboxylate, wherein the enantiomerically enriched carboxylic acid ester is the (+) enantiomer, and wherein the biocatalyst is selected from *Corynebacterium hoagii* ATCC 7005, *Flavobacterium* sp. ATCC 27551, *Pseudomonas oleovorans* NRRL-B-3429, *Pseudomonas putida* ATCC 23973, *Pseudomonas* sp. NRRL-B-11330, *Rhodococcus equi* ATCC 14887, *Rhodococcus erythropolis* ATCC 4277, *Rhodococcus coprophilus* NRRL-B-16536, *Rhodococcus rhodnii* NRRL-B-16535, *Rhodococcus rhodochrous* ATCC 55602, *Rhodococcus* sp. NRRL-B-16531, *Rhodococcus* sp. NRRL-B-16534, *Streptomyces griseus* ATCC 6855, *Xanthomonas campestris* ATCC 21818, *Rhodotorula rubra* ATCC 4557, *Beauveria bassiana* ATCC 26037, *Beauveria bassiana* ATCC 74292, *Beauveria bassiana* ATCC 26851, *Cunninghamella echinulata* ATCC 8688, *Paecilomyces marquandi* ATCC 10525, *Pestalotia microspora* ATCC 11816, *Rhizopus oryzae* ATCC 10404, *Rhizopus oryzae* ATCC 22580, *Trichophyton concentricum* ATCC 74293 and Chirazyme L-7 lipase.

4. The process of claim 2 wherein the mixture of enantiomeric esters of Formula I is methyl-5-chloro-2,3-dihydro-2-hydroxy-1-oxo-1H-indene-2-carboxylate, and the enantiomerically enriched carboxylic acid ester is the (−) enantiomer, and wherein the biocatalyst is selected from *Candida guilliermondii* ATCC 6260, *Candida kefyr* ATCC 4135, *Candida tropicalis* ATCC 46491, *Aspergillus alliaceus* ATCC 10060, *Beauveria nivea* ATCC 74294, *Lophotrichus martinii* ATCC 11221, Sporobolomyces sp. ATCC 20290, *Bacillus cereus* NRRL-B-14591, Nocardia sp. NRRL-B-5646, *Pseudomonas putida* ATCC 17453, *Schizosaccharomyces ostosporus* NRRL-Y-854, *Aspergillus alliaceus* NRRL-315, *Penicillium chrysogenum* ATCC 10002, *Penicillium notatum* ATCC 36740, SP 524 lipase, SP 526 lipase, SP 539 protease, Chirazyme L-2 lipase and Chirazyme L-5 lipase.

5. The process of claim 2 wherein the mixture of enantiomeric esters of Formula I is ethyl α-hydroxy-α-methyl-4-phenoxybenzene acetate, wherein the enantiomerically enriched carboxylic acid ester is the (+) enantiomer, and wherein the biocatalyst is selected from Pseudomonas sp. NRRL-B-11330, *Rhodococcus equi* ATCC 13556, *Candida tropicalis* ATCC 46491, *Aspergillus candidus* ATCC 20022, *Beauveria bassiana* ATCC 26851, *Beauveria bassiana* ATCC 38657, *Mycotypha microspora* ATCC 8982, *Tricophyton concentricum* ATCC 74293, IM60 Lipozyme, SP 524 lipase, SP 526 lipase, Lipolase lipase and CR Lipase.

6. The process of claim 2 wherein the mixture of enantiomeric esters of formula I is ethyl α-hydroxy-α-methyl-4-phenoxybenene acetate, wherein the enantiomerically enriched carboxylic acid ester is the (−) enantiomer, and wherein the biocatalyst is selected from *Amycolatopsis rugosa* NRRL-B-2295, and *Streptomyces endus* NRRL-B-2339.

7. The process of claim 1, further comprising the additional step of separating the enantiomerically enriched carboxylic acid ester from the biocatalytic reaction mixture.

8. The process of claim 7, where said separation is accomplished by extraction or phase separation.

9. A process for the preparation of a mixture enriched in the (+) enantiomer of a carboxylic acid ester which comprises contacting a mixture of enantiomeric esters of methyl 5-chloro2,3-dihydro-2-hydroxy-1-oxo-1H-indene-2-carboxylate with a biocatalyst, wherein the biocatalyst is selected from α-chymotrypsin, β-chymotrypsin, γ-chymotrypsin, and δ-chymotrypsin.

10. The process of claim 9, further comprising the additional step of separating the enantiomerically enriched carboxylic acid ester from the biocatalytic reaction mixture.

11. The process of claim 10, where said separation is accomplished by extraction or phase separation.

\* \* \* \* \*

UNITED STATES PATENT AND TRADEMARK OFFICE
CERTIFICATE OF CORRECTION

PATENT NO. : 5,580,783
DATED : December 3, 1996
INVENTOR(S) : Sariaslani et al.

It is certified that error appears in the above-identified patent and that said Letters Patent is hereby corrected as shown below:

Column 1, Line 46, change "et at" to read --- et al ---.

Column 9, Table 1, change "Cunninghamella echinulata ATCC 8688$^a$" to read as --Cunninghamella echinulata ATCC 8688a--.

Column 15, Line 29, change "enantomer" to read --enantiomer--.

Column 16, Line 11, change "8688" to read --8688a--.

Column 16, Line 26, change "$C_3$" to read --$C_3$ alkyl--.

Column 16, Line 58, change "8688" to read --8688a--.

Signed and Sealed this

Twenty-eighth Day of July, 1998

Attest:

BRUCE LEHMAN

*Attesting Officer*   *Commissioner of Patents and Trademarks*